United States Patent [19]
Bailey

[11] Patent Number: 5,843,038
[45] Date of Patent: Dec. 1, 1998

[54] FINDER-THINWALL NEEDLE COMBINATION FOR SAFELY INSERTING A CATHETER INTO A CENTRAL VEIN

[75] Inventor: John S. Bailey, Irvine, Calif.

[73] Assignee: University of Southern California, Los Angeles, Calif.

[21] Appl. No.: 550,828

[22] Filed: Oct. 31, 1995

[51] Int. Cl.⁶ .................................................. A61M 5/18
[52] U.S. Cl. .......................................... 604/158; 604/165
[58] Field of Search ..................... 604/158, 161, 604/164, 167, 162, 165, 170, 171, 173

[56] References Cited

U.S. PATENT DOCUMENTS

| | | | |
|---|---|---|---|
| 2,630,803 | 3/1953 | Baran | 604/158 |
| 3,840,008 | 10/1974 | Noiles | 604/158 X |
| 4,192,306 | 3/1980 | Genese . | |
| 4,627,841 | 12/1986 | Dorr | 604/158 |
| 4,700,694 | 10/1987 | Shishido | 604/158 X |
| 4,721,506 | 1/1988 | Teves | 604/158 X |
| 4,808,156 | 2/1989 | Dean . | |
| 4,808,168 | 2/1989 | Warring | 604/158 |
| 4,846,799 | 7/1989 | Tanaka et al. | 604/158 |
| 5,057,085 | 10/1991 | Kopans | 604/158 X |
| 5,106,376 | 4/1992 | Mononen et al. | 604/158 X |
| 5,242,411 | 9/1993 | Yamamoto et al. . | |
| 5,290,246 | 3/1994 | Yamamoto et al. . | |
| 5,312,375 | 5/1994 | Gurmarnik | 604/158 X |
| 5,407,431 | 4/1995 | Botich et al. . | |
| 5,611,778 | 3/1997 | Brinon | 604/158 X |

FOREIGN PATENT DOCUMENTS

| | | |
|---|---|---|
| 92/100670.6 | 1/1992 | European Pat. Off. . |
| 94/306641.5 | 9/1994 | European Pat. Off. . |

Primary Examiner—Michael A. Brown
Attorney, Agent, or Firm—Oppenheimer Wolff & Donnelly LLP

[57] ABSTRACT

An apparatus according to the present invention is a finder-thinwall needle combination for central venous catheterization. The finder needle is slidably mounted in very close proximity to or coaxially with the thinwall needle. The tip of the finder needle initially extends a distance beyond the end of the thinwall needle, so that a technician may locate a central vein with the finder needle without significantly damaging a central artery. Then the technician may slide the thinwall needle forward along the finder needle into the vein. The present invention also encompasses a method for inserting a thinwall needle into a central vein without damaging a central artery. First, a technician finds a central vein with the sharp end portion of the finder needle. She then slides the thinwall needle forward relative to the finder needle such that the tip of the thinwall needle enters the vein. The technician then slides the finder needle back along the thinwall needle and out of the vein, thereby leaving the tip of the thinwall needle in the vein.

16 Claims, 5 Drawing Sheets

FINDER-THINWALL NEEDLE COMBINATION FOR SAFELY INSERTING A CATHETER INTO A CENTRAL VEIN

FIELD OF THE INVENTION

The present invention relates to central venous catheters and, more particularly, to an apparatus and method for inserting a catheter into a central vein without damaging a corresponding artery.

BACKGROUND OF THE INVENTION

A common medical procedure is the placement of a catheters into a central vein of a patient, particularly in the groin, chest or neck. The catheter provides a direct route for infusing medication and/or other medical fluids into the patient's bloodstream. Catheters are widely used for repeatedly medicating seriously ill patients, such as those with AIDS and cancer, and are used in special operating procedures. For instance, a surgeon may feed pressure measurement equipment through a central venous catheter such as a Swan-Gans catheter to measure the blood pressure at various points in the heart and lungs.

Various techniques have evolved for placing a catheter in a central vein. At one time, a doctor had to perform a surgery in an operating room to place the catheter. The doctor would make a skin incision about 2 inches long so that he could find the central vein. He would then insert a very large needle into the vein, and would insert the catheter into the vein through the needle. The doctor would then pull the needle back over the catheter and suture the skin.

This old technique had two serious disadvantages. The first was that the surgery had to be done in operating room with anesthesia, and the surgery left a large incision that had to heal. Secondly, the large incision could become infected.

An improved technique, known as the Seldinger technique, evolved in the 1960's and had several steps. Referring to FIG. 1, the technician would place an apertured pad 50 over the area where the catheter was to be inserted. The technician would insert a small finder needle 52 (FIG. 2) with a syringe attached into the skin until she found a central vein 54. She would leave the small finder needle 52 in the vein and remove the syringe, so that the finder needle stuck out of the patient's skin. The technician would then put a larger, hollow thinwall needle 56 into the vein a spaced distance from the finder needle. She then pulled the small finder needle 52 out of the skin, removed the syringe from thinwall needle and fed a soft, flexible wire through the thinwall needle into the vessel.

The technician backed the thinwall needle over the wire and out of the skin, leaving the wire in the vein. She would then make a small incision of about ⅛ inch (a "skin nick"), and would feed a tissue expander and catheter over the wire into the central vein. After she had removed the wire and the tissue expander, the catheter was ready for use.

The Seldinger technique has several advantages over the old surgical method. A technician can perform the Seldinger technique in a hospital room under local anesthesia rather than in an operating room, and the technique does not leave a large incision in the skin. Furthermore, the doctor can inadvertently hit an artery with the finder needle without any serious complications.

Unfortunately, the Seldinger technique also has a serious disadvantage in that the thinwall needle is sometimes inadvertently placed in an artery 58 (FIG. 2) rather than in a central vein 54. The goal of the procedure, of course, is to place the catheter in a central vein 54, which has low blood pressure (about 5–10 mm of mercury). However, running along side every central vein is an artery 58, where blood pressure is high (about 100 mm of mercury). Furthermore, the vein 54 does not always run in the direction that the doctor supposes, and a central vein 54 and associated artery 58 can be twisted around each other, as FIG. 2 illustrates. Consequently, even when the doctor finds a vein with the finder needle, a thinwall needle placed near the finder needle can actually be hitting the artery. This sort of artery puncture occurs in approximately 2.8% of Seldinger procedures. (F. Mihm and M. Rosenthal, Central Venous Catheterization, in CLINICAL PROCEDURES IN ANESTHESIA AND INTENSIVE CARE 366 (Jonathan L. Benumof, ed.))

It is noted that the tip of a finder needle of approximately 21 gauge has a small cross-sectional area and rarely damages an artery upon puncture. However, the cross-sectional area of a needle increases dramatically by the square of the needle's radius. Consequently, a typical thinwall needle of about 18 gauge or less can cause serious damage to the wall of a major artery. The severity and consequences of the damage depends on which area of the body the catheter is being placed. If the doctor damages an artery in the groin, the doctor must hold pressure on the artery for about 10 minutes to stop the bleeding, but otherwise there is usually little damage.

However, when the damage is to an artery in the chest (typically underneath the clavicle), the doctor cannot simply apply pressure to the artery because the collar bone is in the way. The doctor must then operate on the artery to repair it. Subclavian (chest) artery puncture happens approximately 1% of the time with the Seldinger technique. Bleeding from subclavian artery puncture can cause massive hematoma, hemothorax, and bleeding from the skin. Occasionally, someone dies from this bleeding. (Central Venous Catheterization, supra, at 366).

The Seldinger technique can cause even greater problems when a doctor is inserting a catheter into the neck, where 45% of central venous catheters are placed. The internal carotid artery carries a large flow of blood under heavy pressure to the brain. When the thinwall needle of the Seldinger technique punctures the internal carotid, a hematoma forms. The doctor is not able to apply pressure to the artery to stop the bleeding, which would stop or slow blood flow to the brain. Meanwhile, the region around the damaged artery can swell enough to move the airway or block it. Additionally, a blood clot can break loose and flow to the brain, causing stroke.

There are at least three other problems associated with the Seldinger technique. First, it is sometimes difficult to know whether the thinwall needle has hit a central vein or an artery. A common way of checking is to remove the syringe from off of the needle. If the blood spurts out, the doctor knows that the blood is under high pressure and that the thinwall needle has hit an artery. The spurting blood poses a danger to staff in the operating room, particularly when the patient has AIDS or another dangerous blood-born disease.

Secondly, there is always a risk of nerve damage when the thinwall needle misses a vein. Thinwall needles have been known to damage nerves such as the brachial plexus, the phrenic nerve, the cervical sympathetic trunk, the recurrent laryngeal and the vagus. Nerve damage can cause a variety of problems, including sensory-motor loss, paralyzed diaphragm, Horner's syndrome, and hoarseness. (Central Venous Catheterization, supra, at 369–70).

Thirdly, technicians sometimes become impatient with the Seldinger technique and try to save time by using the thinwall needle directly, without using the finding needle first. The probability of hitting an artery rather than the intended vein greatly increases when the technician uses no finder needle at all.

SUMMARY OF THE INVENTION

Generally speaking, an apparatus according to the present invention is a finder-thinwall needle combination for central venous catheterization. The finder needle is slidably mounted in very close proximity to the thinwall needle. The tip of the finder needle initially extends a distance beyond the end of the thinwall needle, so that a technician may safely locate a central vein with the finder needle without significantly damaging a central artery if the technician accidentally punctures the artery. Then the technician may slide the thinwall needle forward along the finder needle into the vein.

This apparatus overcomes the drawbacks of the prior art in a number of ways. First, once the finder needle locates a vein, there is little or no chance that the thinwall needle will then puncture an artery. Consequently, the apparatus is much safer for patients and limits the likelihood that a surgery will have to be delayed until an accidentally-punctured artery heals.

Secondly, the apparatus is convenient to use, and an impatient technician will not be tempted to use the thinwall needle alone. Thirdly, the apparatus is safer for medical personnel, who are less likely to be sprayed with blood while checking to see if the thinwall needle has punctured an artery.

An apparatus according to the present invention may have various other features. The finder needle may include a locator mark for indicating when the thinwall needle has slid sufficiently forward relative to the finder needle for the thinwall needle to have entered the central vein. The thinwall needle may have a gauge of approximately 18 or less, and the finder needle may have a gauge of approximately 20 or higher.

The thinwall and finder needles may be mounted coaxially, or may be mounted side-by-side. In the coaxial embodiment, the thinwall and finder needles may both have fittings so that the two needles may releasably engage while the technician is searching for the vein. Then, when the technician has located the vein with the finder needle, the two needles may gently disengage so that the thinwall needle may slide into the vein. The thinwall needle may further include butterfly wings that a technician may grasp to slide the thinwall needle forward on the finder needle.

Furthermore, in certain embodiments of the invention, the finder needle may initially extend a distance of at least 1 inch beyond the end of the thinwall needle, to give the technician an ample length of finder needle with which to locate a central vein. In other embodiments, the finder needle may initially extend more or less than one inch beyond the end of the finder needle, depending on the area of the body that the catheter is to be placed and on the size of the patient.

The present invention also encompasses a method for inserting a thinwall needle into a central vein without damaging a central artery. The thinwall needle is initially provided in a finder-thinwall needle combination comprising a thin finder needle mounted in close proximity to the thinwall needle. The sharp end of the finder needle initially extends beyond the tip of the thinwall needle.

The method includes several steps. First, a technician finds a central vein with the sharp end portion of the finder needle. She then slides the thinwall needle forward relative to the finder needle such that the tip of the thinwall needle enters the vein. The technician then slides the finder needle back along the thinwall needle and out of the vein, thereby leaving the tip of the thinwall needle in the vein.

Various embodiments of the method may include additional steps. In a presently preferred embodiment, the finder and thinwall needles are substantially coaxially mounted. The finder-thinwall needle combination may further include a syringe mounted on the finder needle. The step of finding a central vein may include piercing a central vessel with the finder needle and aspirating the syringe to partially fill the syringe with blood. The technician can determine from the color of the blood whether the finder needle has struck a vein or an artery.

The finder needle may also include a locator mark, and the step of sliding the thinwall needle forward relative to the finder needle may further include sliding the thinwall needle forward until a portion of the thinwall needle is aligned with the locator mark.

To insure that the finder needle is thin enough so as not to damage an artery, the finder needle may have a gauge of approximately 20 or higher. Similarly, to insure that the interior of the thinwall needle is sufficiently wide to permit a wire to pass through, the thinwall needle may have a gauge of approximately 18 or less.

Other objects, features, and advantages of the invention will become apparent from a consideration of the following detailed description and the accompanying drawings.

DETAILED DESCRIPTION OF THE PREFERRED EMBODIMENT

Figure 1:
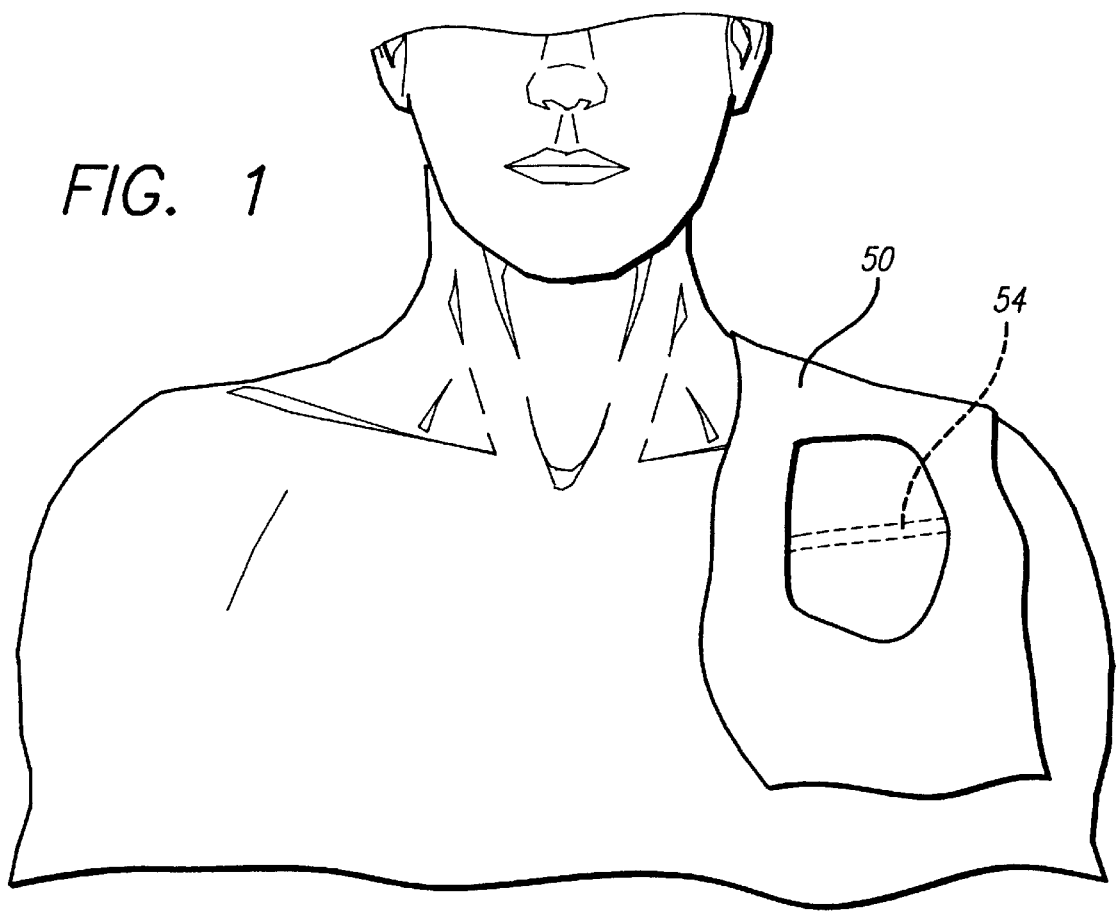
FIG. 1 illustrates an apertured pad placed over the portion of the chest where the subclavian vein is to be found.
Figure 2:
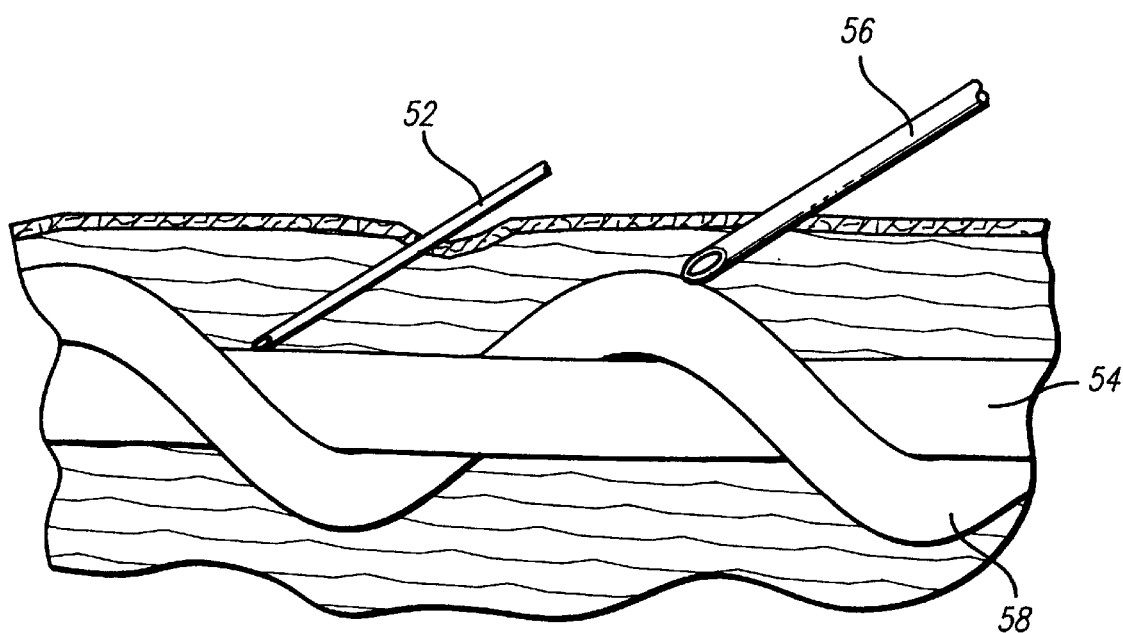
FIG. 2 illustrates one problem of the prior art Seldinger technique, in which the finder needle locates a central vein but the thinwall needle punctures an artery nearby.
Figure 3:
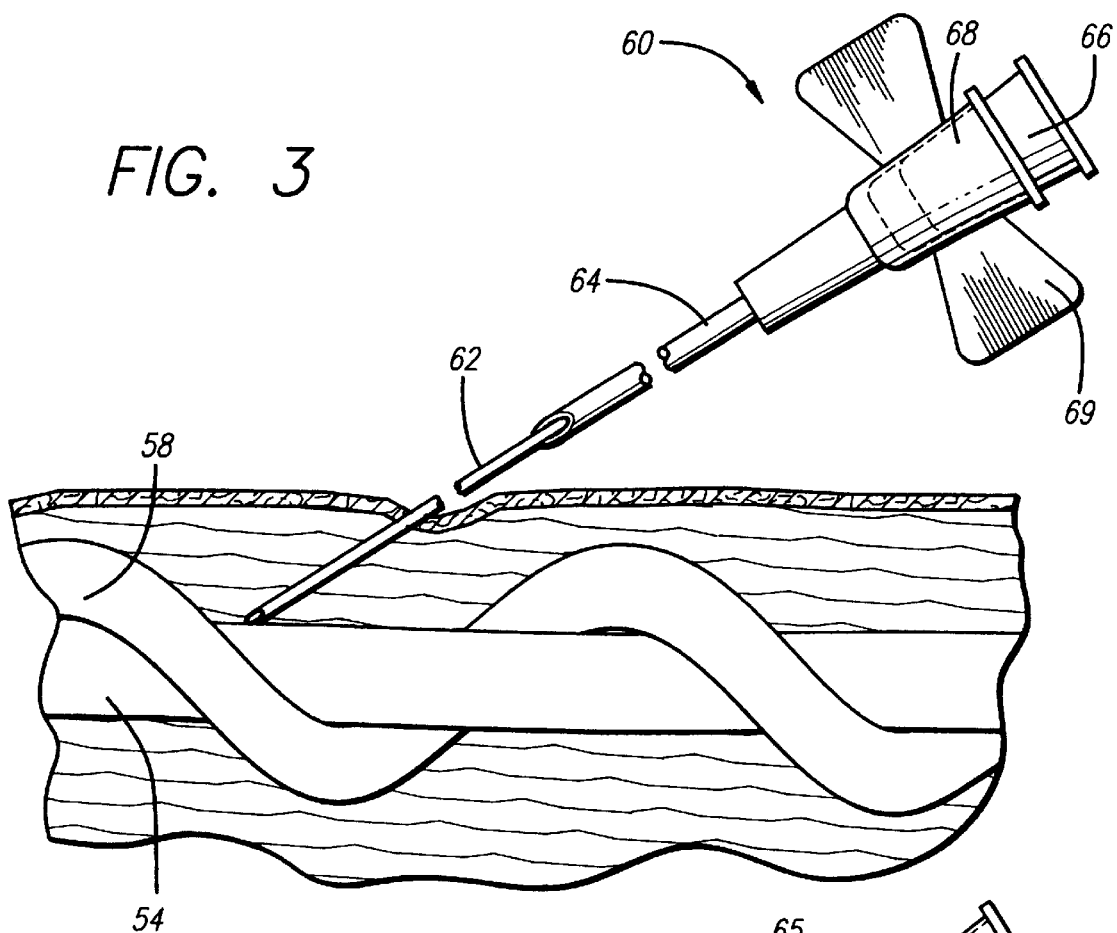
FIG. 3 is a perspective and partial-sectional view of a finder-thinwall needle combination, with the finder needle about to enter a central vein.

FIG. 3 illustrates a coaxial needle assembly 60 having a thin finder needle 62 loaded coaxially on a thinwall needle 64. The finder needle 62 is substantially longer than the thinwall needle 64. Male and female luer slips 65, 66, also called "slip tips", are mounted on the hub of the finder needle. The male luer slip 65 mates with another female luer slip 68 on the hub of the thinwall needle. The luer slips 65 and 68 allow the two needles to softly slip together and to releasably engage as in FIG. 3, and also to allow the user to smoothly disengage the needles as in FIG. 4. The luer slip 68 may include optional butterfly wings 69 for a technician to grasp when sliding the thinwall needle 64 relative to the finder needle 62.

The coaxial needle assembly 60 is used in an improved, safer method of inserting a catheter into a central vein. In the first step, a technician inserts the finder needle 62 of the coaxial needle assembly 60 into a blood vessel 54 in FIG. 3. A syringe is attached to the finder-thinwall assembly at the luer slip 66, and the technician aspirates the syringe to get blood flow into the syringe. If the blood is generally bright red, the technician knows that the finder needle has hit an artery. However, if the blood is generally bluish, the finder needle has hit a vein.

Figure 4:
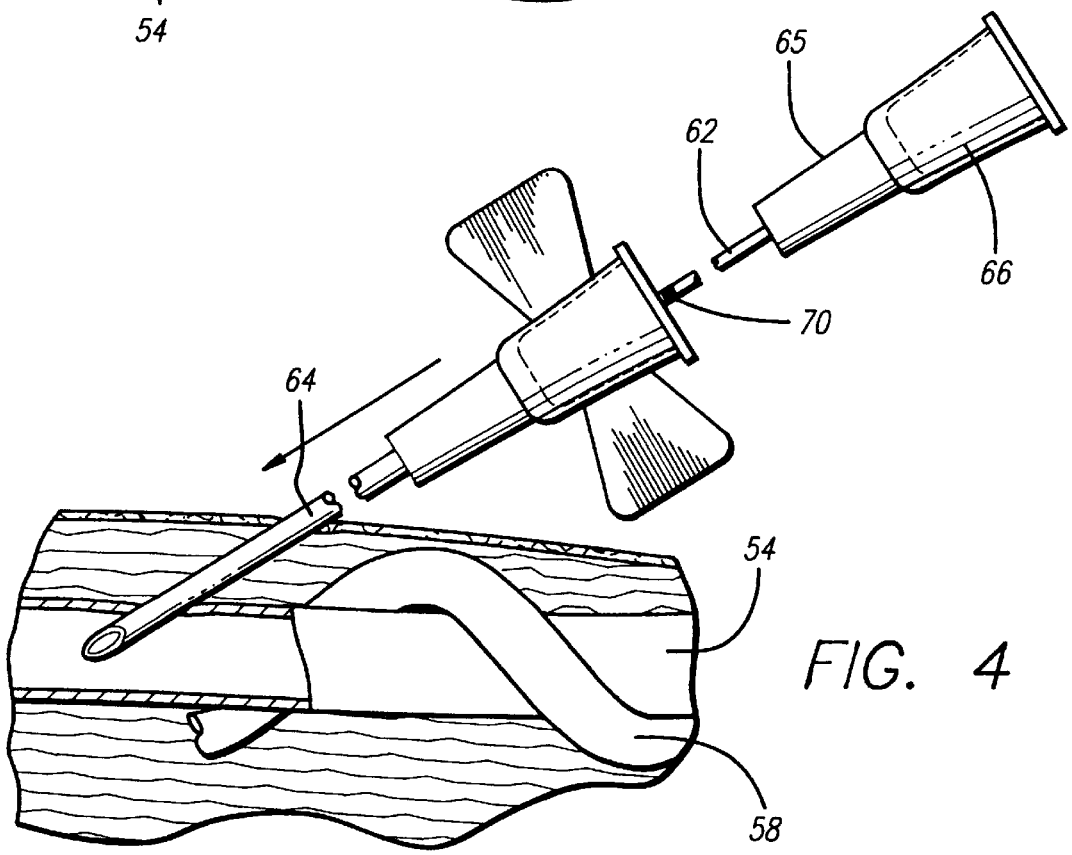
FIG. 4 illustrates the thinwall needle having been slid forward relative to the finder needle into the vein.
Figure 5:
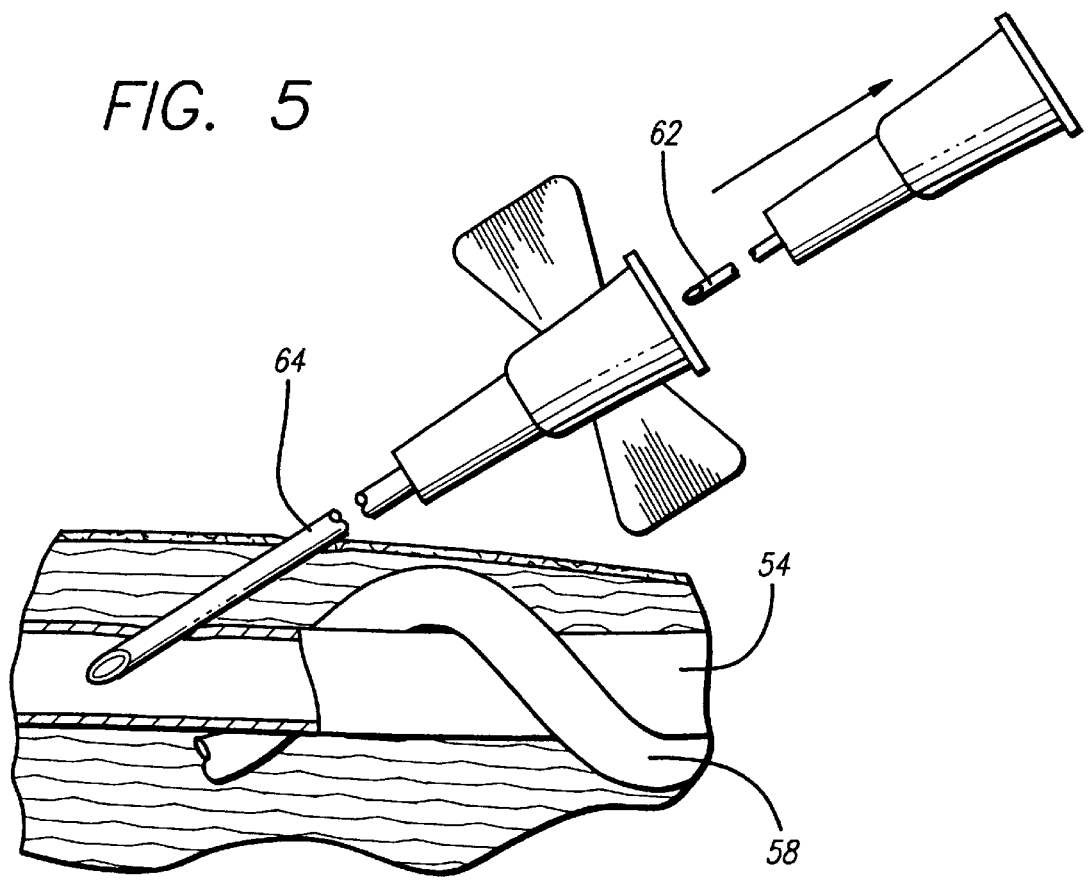
FIG. 5 illustrates the finder needle sliding backward out of the vein, leaving the thinwall needle alone in the vein.
Figure 6:
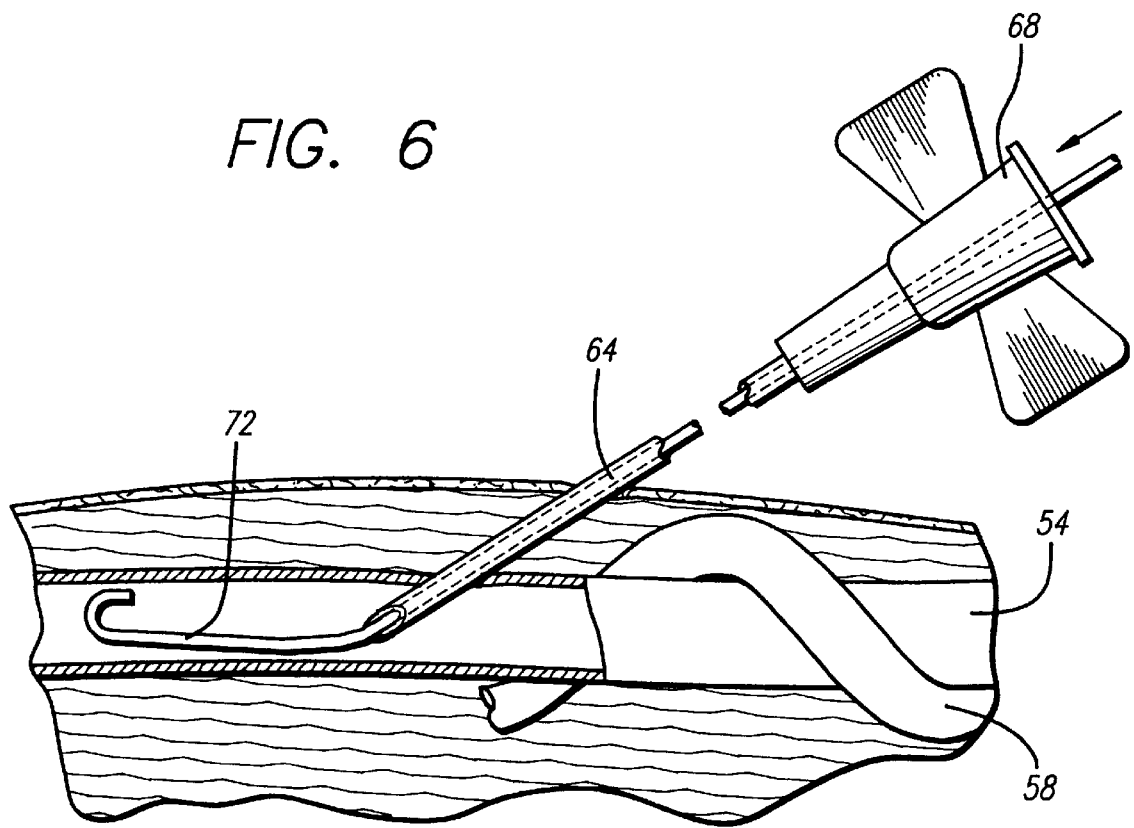
FIG. 6 illustrates a wire fed through the thinwall needle and into the vein.
Figure 7:
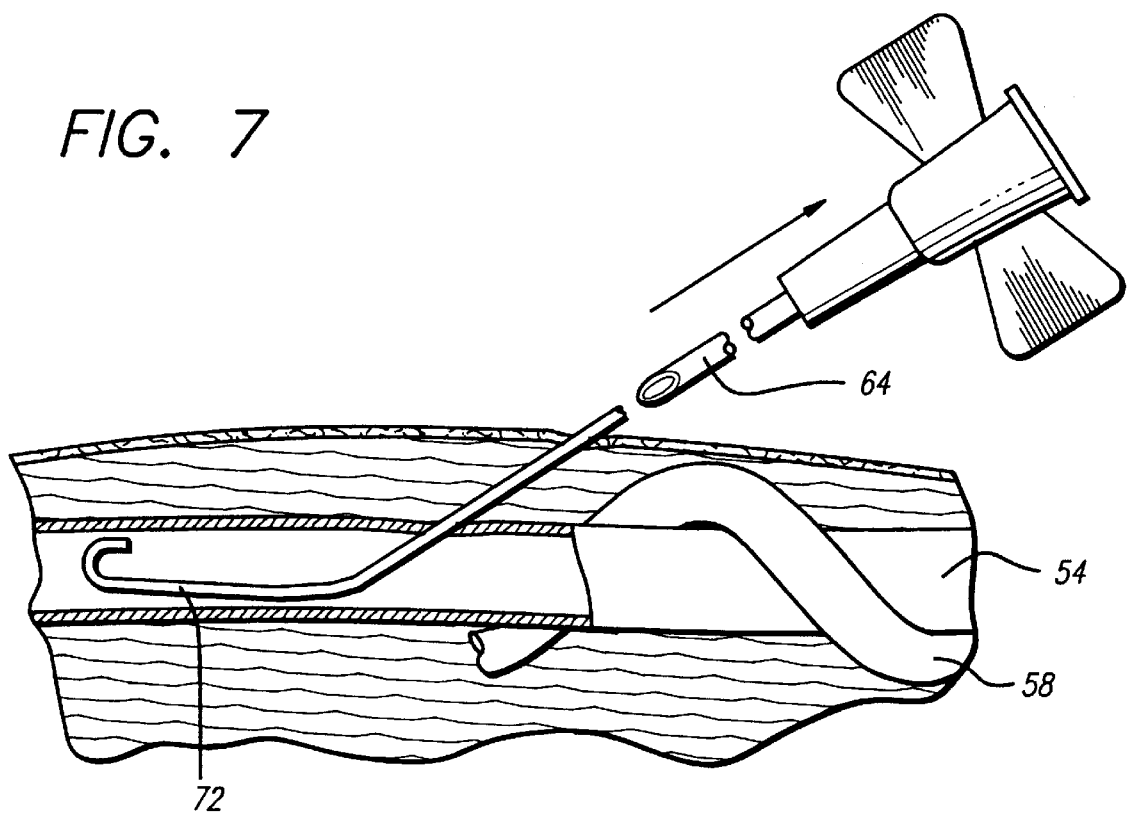
FIG. 7 illustrates the thinwall needle being pulled out of the vein, leaving the wire alone in the vein.
Figure 8:
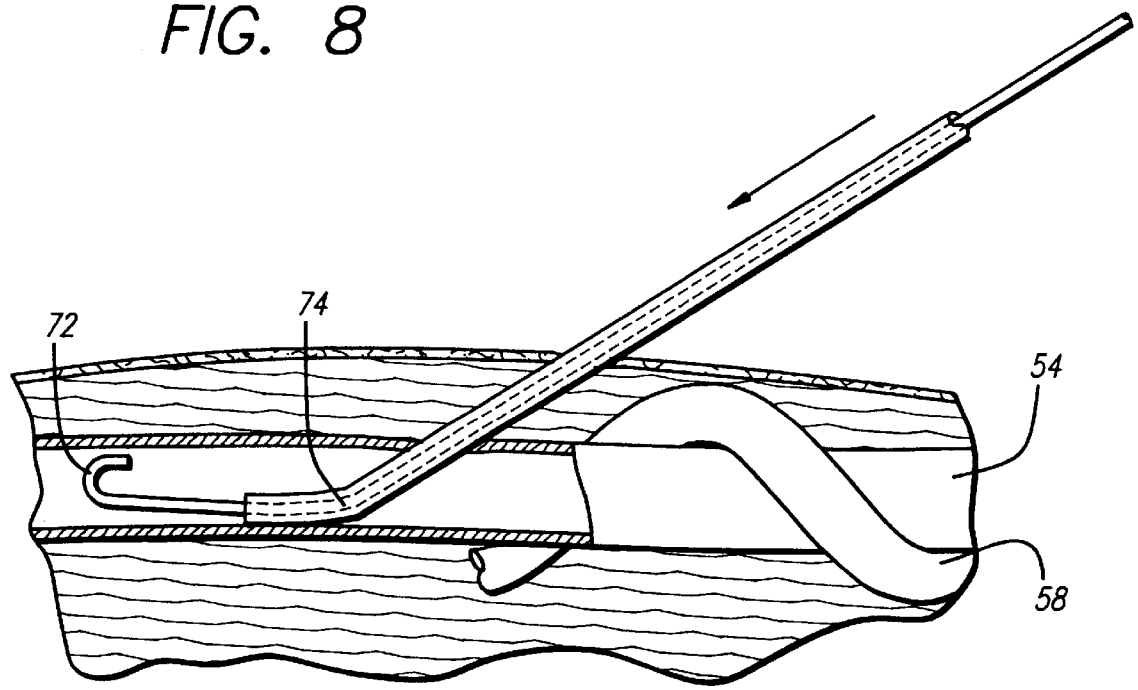
FIG. 8 illustrates a catheter being slid over the wire and into the vein.

When the technician determines that the finder needle has found a vein, he slides the thinwall needle 64 down the finder needle 62 until the mark 70 on the shaft of finder needle shows, as in FIG. 4. The technician then removes the finder needle 62 (FIG. 5) and runs a wire 72 through thinwall needle into the vein (FIG. 6). After sliding the thinwall needle over the wire and out of the vein (FIG. 7), the technician slides a catheter 74 down the wire and into the vein (FIG. 8).

Figure 9:
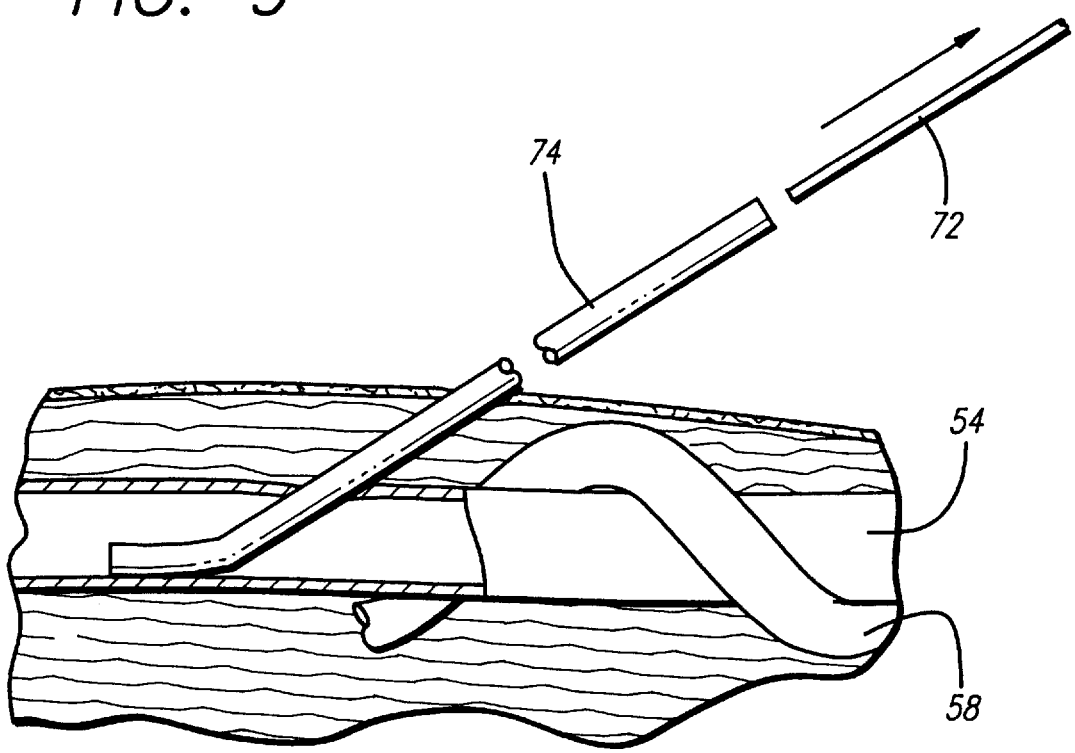
FIG. 9 illustrates the wire being pulled through the catheter out of the vein.

It should be noted that the catheter may be coaxially loaded onto a tissue expander, which slides down the wire with the catheter to open a passage for the catheter. Once the catheter is in place in the vein, the tissue expander and wire are pulled through the catheter (FIG. 9). A medical technician, a doctor or the patient himself may then infuse medical fluids directly into the vein through the catheter.

There are several advantages to the present method as compared to the standard Seldinger approach. First, the present method removes an entire step from the Seldinger technique. The technician does not need to find and puncture the vein twice in two different areas. Secondly, the technician does not need to use a syringe with the thinwall needle to check that the thinwall needle is properly placed. As there is little or no chance of arterial puncture with the (large) thinwall needle, there is no dangerous blood spray when checking placement of the thinwall needle. Thirdly, the method of the present invention is easier to implement than the Seldinger technique, is safer for the patient, and is performed with an inexpensive coaxial needle assembly.

By way of example of one particular embodiment, and not by way of limitation, a coaxial needle assembly 60 may have the following illustrative dimensions. The thinwall needle 64 may typically be approximately 18 gauge. The finder needle 62 is generally about 21 gauge. The needles 62 and 64 may be purchased from the Becton-Dickenson Company of New Jersey, although the hub of the finder needle must at present be modified to releasably engage the thinwall needle. In a presently preferred embodiment, the finder needle 62 is 5 inches long and has a 21 gauge diameter The thinwall needle is 2½ inches long with an 18 gauge diameter.

The finder needle 62 preferably will extend at least about ½" from the end of the thinwall needle 64, although it is presently preferred that the finder needle 62 extend beyond the thinwall needle by approximately at least 1"–1¼". An extension of as little as only ¼" may possibly be used, however, although there is very little exposed finder needle with which to find a vein.

In conclusion, it is to be understood that the foregoing detailed description and the accompanying drawings relate to presently preferred embodiments of the invention. Various changes and modifications may be made without departing from the spirit and scope of the invention. Thus, by way of example and not of limitation, both needles may be substantially shorter than those illustrated, for use on particular parts of the body and/or for use with small patients such as infants.

The two needles could fit together in a number of ways, including by being screwed together. A valve could be added to the thinwall needle to prevent blood flow back through the thinwall needle as the finder needle is pulled out.

As a further alternative embodiment, a catheter may be provided over the finder needle, such that once the finder needle has located a vein, the catheter slides over the finder needle directly into the vein. Furthermore, various types of catheters, including multiple lumens catheters, may be used in conjunction with the present apparatus and method.

It is noted that the term "parallel" in the claims includes both "side-by-side" and "coaxial" arrangements.

Accordingly, the present invention is not limited to the specific embodiments shown in the drawings and described in the detailed description.

What is claimed is:

1. A method for inserting a thinwall needle into a central vein without damaging a central artery, the thinwall needle being initially provided in a finder-thinwall needle combination comprising a thin finder needle mounted substantially coaxially within the thinwall needle, with a sharp end portion of the finder needle initially extending beyond the tip of the thinwall needle, the method comprising the steps of:

finding a central vein with the sharp end portion of the finder needle and extending the sharp end portion of the finder needle into the vein;

sliding the thinwall needle forward relative to the finder needle such that the tip of the thinwall needle enters the vein;

sliding the finder needle back relative to the thinwall needle and out of the vein, thereby leaving the tip of the thinwall needle in the vein;

running a wire through the thinwall needle into the vein;

sliding the thinwall needle back along the wire and out of the vein;

sliding a catheter over the wire and into the vein; and removing the wire from the vein, thereby leaving the catheter inserted into the vein.

2. A method for inserting a thinwall needle as defined in claim 1, wherein the finder-thinwall needle combination further includes a syringe mounted on said finder needle, and the step of finding a central vein includes piercing a central vessel with said finder needle and aspirating said syringe to partially fill said syringe with blood to determine if the blood comes from a vein or from an artery.

3. A method for inserting a thinwall needle into a central vein as defined in claim 1, wherein said finder needle includes a locator mark, and the step of sliding the thinwall needle forward on the finder needle further includes sliding the thinwall needle forward until a portion of the thinwall needle is aligned with said locator mark.

4. A method for inserting a thinwall needle into a central vein as defined in claim 1, wherein said thinwall needle has a gage of 18 or less, and wherein said finder needle has a gage of 20 or higher.

5. A method for inserting a catheter into a central vein without damaging a central artery, the method utilizing a finder-thinwall needle combination comprising a thin finder needle mounted in very close proximity to and parallel with the thinwall needle, with a sharp end portion of the finder needle initially extending beyond the tip of the thinwall needle, the method also utilizing a thin wire and a catheter tube, the method comprising the steps of:

finding a central vein with the sharp end portion of the finder needle and extending the sharp end portion of the finder needle into the vein;

sliding the thinwall needle forward relative to the finder needle such that the tip of the thinwall needle enters the vein;

sliding the finder needle back relative to the thinwall needle and out of the vein, thereby leaving the tip of the thinwall needle in the vein;

running a thin wire through the thinwall needle into the vein;

sliding the thinwall needle back along the wire and out of the vein;

sliding a catheter over the wire and into the vein; and removing the wire from the vein, thereby leaving the catheter inserted into the vein.

6. A method for inserting a catheter into a central vein as defined in claim 5, wherein the method further utilizes a tissue expander and the method further comprises the step of running the tissue expander along the thin wire to open the tissue to receive the catheter.

7. A method for inserting a catheter into a central vein as defined in claim 5, wherein the finder needle further includes a locator mark, and the step of sliding the thinwall needle forward relative to the finder needle includes sliding the thinwall needle forward until it aligns with the locator mark.

8. A method for inserting a catheter into a central vein without damaging a central artery, the method utilizing a finder-thinwall needle combination, a wire and a catheter, the method comprising:

providing a finder-thinwall needle combination for central venous catheterization having:

a thinwall needle having a sharp end and an opening at said sharp end; and a finder needle having a sharp tip, said finder needle extending parallel to said thinwall needle;

wherein said sharp tip of said finder needle extends at least ¼" beyond the opening of said thinwall needle;

said thinwall needle has a gage of 18 or less, and wherein said finder needle has a gage of 20 or higher;

finding a central vein with the sharp end portion of the finder needle and extending the sharp end portion of the finder needle into the vein;

sliding the thinwall needle forward relative to the finder needle such that the tip of the thinwall needle enters the vein;

sliding the finder needle back relative to the thinwall needle and out of the vein, thereby leaving the tip of the thinwall needle in the vein;

running a thin wire through the thinwall needle into the vein;

sliding the thinwall needle back along the wire and out of the vein;

sliding a catheter over the wire and into the vein; and removing the wire from the vein, thereby leaving the catheter inserted into the vein.

9. A method as defined in claim 8, wherein:

said thinwall needle further includes a first fitting;

said finder needle includes a second fitting;

said needle combination has a first mode in which said first and second fittings are releasably engaged with one another, with said sharp tip of said finder needle extending at least ¼" beyond the opening of said thinwall needle; and said needle combination has a second mode in which said first and second fittings are disengaged from one another so that said thinwall needle may slide forward to said sharp tip of said finder needle;

whereby said needle combination may be used in said first mode to safely locate a central vein, then used in said second mode to insert said thinwall needle into the central vein without damaging a central artery.

10. A method as defined in claim 8, wherein thinwall needle further includes butterfly wings that a technician may grasp to slide said thinwall needle forward on said finder needle.

11. A method as defined in claim 8, wherein said finder needle includes a locator mark for indicating when said thinwall needle has slid sufficiently forward on said finder needle for said thinwall needle to have entered the central vein.

12. A method as defined in claim 8, wherein said finder needle has a second end adapted to receive a syringe, such that when said finder needle is inserted into a central blood vessel, a technician may aspirate and partially fill the syringe with blood to determine whether said finder needle is properly lodged in a vein rather than in an artery.

13. A method as defined in claim 8, wherein said finder needle is at least 3 inches long, and wherein said thinwall needle is at least 2 inches long, such that said sharp tip of said finder needle may extend at least one inch beyond the opening of said thinwall needle.

14. A method as defined in claim 8, wherein said finder needle and said thinwall needle are both predominantly metal.

15. A method as defined in claim 8, wherein said finder needle is mounted coaxially with said thinwall needle.

16. A finder-thinwall needle combination with a guide wire and a catheter for central venous catheterization comprising:

a thinwall needle having a sharp end and an opening at said sharp end;

a finder needle having a sharp tip, said finder needle extending in parallel to said thinwall needle;

wherein said sharp tip of said finder needle extends at least ¼" beyond the opening of said thinwall needle;

said thinwall needle further including a first fitting;

said finder needle including a second fitting;

said needle combination having a first mode in which said first and second fittings are releasably engaged with one another, with said sharp tip of said finder needle extending at least ¼" beyond the opening of said thinwall needle;

said needle combination having a second mode in which said first and second fittings are disengaged from one another so that said thinwall needle may slide forward to said sharp tip of said finder needle;

said finder needle being at least 3 inches long, and said thinwall needle being at least approximately 2 inches long, such that said sharp tip of said finder needle may extend at least one inch beyond the opening of said thinwall needle;

a catheter; and a catheter guide wire that is adapted to extend through said thinwall needle when said thinwall needle is inserted into the central vein and to extend through said catheter when said catheter is slid onto said wire;

wherein said thinwall needle has a gage of 18 or less, and said finder needle has a gage of 20 or higher; and a technician may locate a central vein with said finder needle without significantly damaging a central artery, and the technician may then slide said thinwall needle forward along said finder needle to place said thinwall needle into the vein, then slide said guide wire through said thinwall needle and into the vein, and then slide said catheter over said guide wire and into the vein.

* * * * *